United States Patent
Effenhauser et al.

(10) Patent No.: US 9,063,038 B2
(45) Date of Patent: Jun. 23, 2015

(54) BENT MICROSTRUCTURES FOR SAMPLING, TRANSPORTING OR DISPENSING A FLUID MEDIA

(71) Applicant: Roche Diagnostics Operations, Inc., Indianapolis, IN (US)

(72) Inventors: Carlo Effenhauser, Weinheim (DE); Patrick Griss, Otelfingen (CH); Stephan Korner, Cham (CH); Emad Sarofim, Abtwil (CH)

(73) Assignee: Roche Diagnostics Operations, Inc., Indianapolis, IN (US)

(*) Notice: Subject to any disclaimer, the term of this patent is extended or adjusted under 35 U.S.C. 154(b) by 39 days.

(21) Appl. No.: 13/800,795

(22) Filed: Mar. 13, 2013

(65) Prior Publication Data

US 2013/0183212 A1 Jul. 18, 2013

Related U.S. Application Data

(63) Continuation of application No. 13/439,036, filed on Apr. 4, 2012, now Pat. No. 8,420,024, which is a continuation of application No. 11/791,251, filed as application No. PCT/CH2005/000688 on Nov. 22, 2005, now Pat. No. 8,241,566.

(30) Foreign Application Priority Data

Nov. 22, 2004 (EP) .................................. 04027634

(51) Int. Cl.
*G01N 33/00* (2006.01)
*G01N 1/20* (2006.01)
(Continued)

(52) U.S. Cl.
CPC .......... *G01N 1/20* (2013.01); *Y10T 436/110833* (2015.01); *Y10T 29/49826* (2015.01);
(Continued)

(58) Field of Classification Search
CPC ............. B01J 2219/00387; B01L 2400/0406; B41J 2/1631
USPC ....................... 422/500–503; 436/180; 347/40
See application file for complete search history.

(56) References Cited

U.S. PATENT DOCUMENTS

| | | |
|---|---|---|
| 1,895,727 A | 1/1933 | Pearce |
| 2,030,918 A | 2/1936 | Halpin et al. |
| 3,358,496 A | 12/1967 | Farmer |
| 4,269,197 A | 5/1981 | Gilbard |
| 4,731,335 A | 3/1988 | Brigati |
| 4,789,263 A | 12/1988 | Germann |
| 6,116,297 A | 9/2000 | Feygin |
| 6,602,472 B1 | 8/2003 | Zimmermann et al. |

(Continued)

FOREIGN PATENT DOCUMENTS

EP  1 388 369 A2  11/2004

OTHER PUBLICATIONS

T. Hantschel, L. Wong, C.L. Chua, D.K. Fork; Fabrication of highly conductive stressed-metal springs and their use as sliding-contact interconnects; Microelectronic Engineering; 67-68 (2003) pp. 690-695.

*Primary Examiner* — Jill Warden
*Assistant Examiner* — Brittany Fisher
(74) *Attorney, Agent, or Firm* — Dinsmore & Shohl LLP

(57) ABSTRACT

A device for sampling, transporting and/or disposal of fluid media in the nl and µl-range comprises a substrate with an open or closed capillary-like groove or channel respectively, the substrate with the open or closed groove or capillary respectively is bent or arcuated at least at one location. The substrate comprises at least one end into which the open or closed capillary-like groove or channel respectively is extended, which end is shaped according to its application or use as e.g. needle-like, straight-lined cut, tip-like, at least most half circle-shape, rounded, etc.

18 Claims, 8 Drawing Sheets

(51) Int. Cl.
 *B01L 3/02* (2006.01)
 *B01L 3/00* (2006.01)
(52) U.S. Cl.
 CPC .......... *Y10T436/2575* (2015.01); *B01L 3/0244* (2013.01); *B01L 3/502707* (2013.01); *B01L 3/502715* (2013.01); *B01L 2200/025* (2013.01); *B01L 2400/025* (2013.01); *B01L 2400/0406* (2013.01)

(56) References Cited

U.S. PATENT DOCUMENTS

| | | | |
|---|---|---|---|
| 7,241,420 | B2 | 7/2007 | Hantschel et al. |
| 2003/0183761 | A1 | 10/2003 | Hantschel et al. |
| 2003/0211629 | A1 | 11/2003 | Baumgardner et al. |
| 2004/0022681 | A1* | 2/2004 | Hantschel et al. .............. 422/63 |

* cited by examiner

BENT MICROSTRUCTURES FOR SAMPLING, TRANSPORTING OR DISPENSING A FLUID MEDIA

CROSS REFERENCE TO RELATED APPLICATIONS

This application is a continuation of currently U.S. patent application Ser. No. 13/439,036 filed Apr. 4, 2012, which is a continuation of U.S. Ser. No. 11/791,251, filed May 21, 2007, now U.S. Pat. No. 8,241,566, which is a National Phase Entry of International Application No. PCT/CH2005/000688 filed Nov. 22, 2005, which claims priority to EP Application 04027634.7 filed Nov. 22, 2004.

FIELD OF THE INVENTION

The present invention refers to a device or an instrument respectively for sampling, transporting or dispensing of fluid media according the introduction of claim 1, a microstructure comprising at least a device or facility, the use of the device or the structure as well as a method for the production of a device or structure respectively.

BACKGROUND AND SUMMARY OF THE INVENTION

For sampling or dispensing respectively of fluid samples, such as in particular of fluids in the analytical field such as in particular medical or pharmaceutical field among others so called pipettes or capillaries or multiple pipette microstructures are used. In the course of increasing the efficiency in analytical laboratories, the economization and due to smaller sample amounts in this field also the used instruments such as in particular pipettes or multiple pipette structures are getting finer and more complex. For this purpose e.g. from the firms Zymark or Caliper multiple pipette structures are offered comprising up to 384 so called pipette tips for sampling amounts in the range of 2 to 100 nI.

In the EP 1 388 369 micro fluidic systems are proposed, which can be used in micro array systems including channel spring probes, that include at least one capillary channel. The proposed spring beams with incorporated channels as e.g. stressy metal beams curve away from a substrate when released. The channel spring probes are arranged onto a substrate by using specific production steps by covering the substrate with a plurality of layer coatings, so that the spring properties are achieved.

The subject of the present invention consists in proposing further refinement or increase of capacity and the possibility of increased automation in micro-technical process steps by using Nano- or Microsystems as in particular in analyses, the execution of test series, sampling, sample dispensing, at capillary-electro phoresis, capillary-chromatography, etc., etc.

According the present invention it is proposed, that instead of a "straight" device, a planar 2D-structure or channel spring probes arranged onto a substrate as proposed within the EP 1 388 369, in the nI or µl-range, a bent or arcuate fluidic device or a corresponding fluidic instrument respectively or a 3D-structure is used. E.g. an out of plane sampling device for sampling, transporting and/or disposal of fluid media is proposed, comprising within a substrate plane at least one longitudinal extending strip like portion, comprising a liquid channel, such as a pipette or a capillary tube or needle respectively for sampling or dispensing, which is bent or arcuate designed at least at one location extending out of the plane of the substrate.

"Bent" in the sense of the present invention means that out of an initially, essentially plane substrate, e.g. a substrate pre-structured by etching a three-dimensional structure has been produced by a specific bending action, the bent parts of the initially plane substrate project out of the plane of the substrate. In particular capillary channels or grooves can be produced which either are running into the substrate plane or also out of the substrate plane.

Surprisingly and against any assumption it could be proved in experiments that the flow in e.g. so called capillary grooves and in particular in open fluid channels also works "around the corner" in the µl and nano liter range. The open channel or the open channels can be inside as well as outside of the radius of curvature at the location of the bending.

The same of course is valid for structures, which consist of a plurality of devices or instruments respectively including liquid channels in the micro liter or nano liter range comprising at least one bent location or structure respectively as proposed above.

It goes without saying that the flow characteristic of the fluid within the capillary grooves or fluid channels is dependent on the geometry and the surface finish or coating of the inner wall surface. In case of a water based solution or a fluid the surface is preferably hydrophilic and case of a more oily fluid the surface characteristic is preferably more hydrophobic like. As a general comment, one can say, that the contact angle between the fluid and the surface should be small.

Within the prior art so called 3D-structures are known, where capillaries for sampling are bonded into and/or arranged onto a so called "out-of-plane" structure as e.g. the channel spring probes as proposed in the EP 1 388 369.

For these structures the production costs are very high and also the production method is complicated and error-prone. In addition with some of such structures closed liquid channels have to be used which means within the prior art often so called closed capillaries are proposed. In addition for the spring probes as proposed within the EP 1 388 369 multi structures have to be applied onto a substrate to achieve the spring properties.

In contrast to the today usually used materials for the production of pipettes or capillaries i.e. for the production of the devices proposed according the present invention or structures comprising a plurality of devices or instruments respectively preferably plastically formable material as metals, at least partially plastic polymers and the same are used usually comprising only one layer.

On one side the production of the inventively proposed elements or instruments such as pipettes and capillaries or of whole structures is very simple, as the elements or instruments comprising the fluid channels usually consist only of one layer and can be bent in a simple manner. In addition a metal band can be used as a basis, which can be treated by using well-known lithography processes such as e.g. by means of etching to produce the liquid channels. It is possible e.g. to produce open channels on one side or both sides of a small metal band and further more closed channels can be produced by covering the open channels using a film. The possible production processes for the production of the inventive elements or devices respectively like i.e. etching, punching, bending, etc. shall be explained later on with reference to the attached drawings.

The advantage of the instruments or devices proposed according the present invention is, that sampling or dispensing of a sample is far easier by using a bent or arcuated element, such as a pipette or a capillary including instrument, as it does not have to be moved against the substrate surface in a more or less perpendicularly manner, from which substrate a sample has to be removed. It is e.g. possible to move the pipette or capillary including device from one side more or less in a parallel manner over the surface of the substrate for removing a sample. By using an inventive structure also at limited dimensional conditions at the same time a plurality of samples can be removed or dispensed in a simple manner. The various advantages of the inventively proposed devices or elements respectively as well as the structures shall be explained in more details later on with reference to the attached drawings.

Furthermore a process is described for sampling, transporting and/or dispensing of fluid media in particular by using the above mentioned devices or the above mentioned structures. According to the inventive process a pipette or capillary such as a needle or a structure, comprising a plurality of pipettes or capillaries is used and the fluid is transported along a location at sampling or dispensing a sample, which is arcuated or bent respectively.

Further preferred aspects or embodiments of the elements, devices as well as of the structures and the processes respectively are characterized in dependent claims.

The devices, instruments or structures respectively according the present invention are suitable in particular for diagnostic or analytical processes in the field of chemistry, medicine, microbiology, pharmaceutics, etc. The invention shall be explained in more details with reference to the attached drawings.

BRIEF DESCRIPTION OF THE DRAWINGS

In the drawings:

FIG. 17a shows a micro fluidic-device with bent distance elements, and FIG. 17b a stack of a plurality of micro fluidic-devices as shown in FIG. 17a.

DETAILED DESCRIPTION

Figure 1:
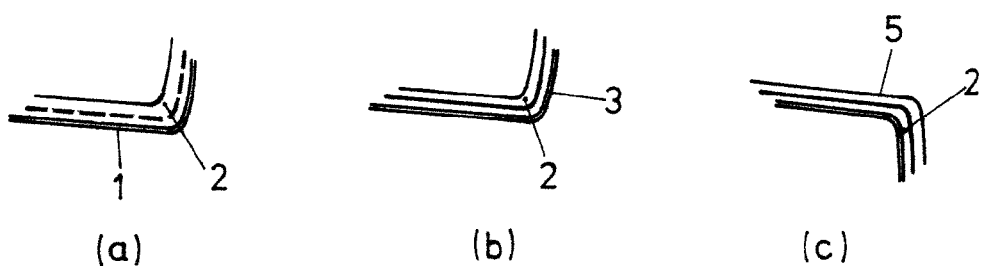
FIG. 1a-1c show in perspective view embodiments of a bent fluidic channel.

In the FIGS. 1a to 1c schematically and in perspective view three embodiments are shown, how a fluidic channel can be arranged on an individual fluidic element "around-the-corner" of an inventive fluidic structure. FIG. 1a shows a bent element 1 comprising two layers with a closed channel, comprising a bend 2.

FIG. 1b shows a one layer bent element 3 comprising an open "inner" channel with a bend of e.g. approximately 90 degrees.

FIG. 1c finally shows a one layer bent element 5, comprising an "outer" open channel and a bend 2.

FIGS. 2a and 2b show each a bent element, which is needle-like shaped. FIG. 2a shows a bent needle-shaped element 7 with an inner open channel and a needle-shaped tip 6. FIG. 2b shows a bent needle-shaped element 9 with an outer open channel and a needle-shaped tip 10. The bent fluidic elements shaped as a needle can be used for sampling from a well-plate or for the direct sampling of body fluids or the dispense of a fluid into a human or animal body by piercing.

The bent or arcuate fluidic element can also be shaped as a tip end, as shown in the FIGS. 3a and 3b. FIG. 3a again shows a bent tip 11 with an inner open channel and an even cut tip end 12 while FIG. 3b shows a bent tip 13 with an outer open channel comprising an even cut tip end 14. Again the tip-like element can be used for sampling from a well-plate. The tip end has only to be dipped into a fluid and the capillary is filled automatically. Of course other forms or designs of a tip or needle-like element are possible such as e.g. elements comprising a semi-circle shaped end, comprising ends with a wave-structure, the end-areas of the elements may comprise a capillary or a plurality of capillaries which may be closed or open, as described above.

With the use of experiments it could be shown, that the flow "around the corner" in particular also with use of open fluid channels works perfectly. It is irrelevant, if the open channel (capillary) is on the inner or the outer surface of the bent radius.

Figure 3:
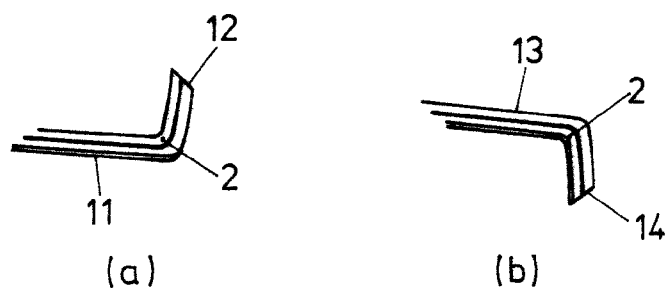
FIGS. 3a and 3b show in perspective view a bent element, comprising a tip-like end, FIGS. 4a and b liquid reservoirs in perspective view as well as fluidic elements for sampling.
Figure 4A:
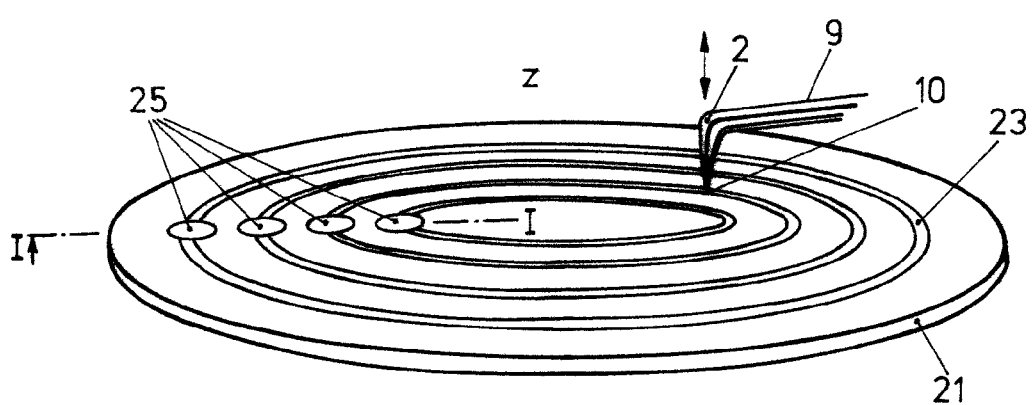
FIG. 4c shows a section along line I-I of FIG. 4a and b.

In FIG. 4a schematically and in perspective view a well-plate disk 21 as liquid source is shown with open grooves 23 arranged corresponding to the circle-round disk as closed circles. The open grooves 23 are fed through so-called well-reservoirs 25. The sampling or disposal of samples by use of the fluidic elements as shown e.g. in FIGS. 1 to 3 can happen in the following manner: a flat disk, as the well-plate-disk 21 with open grooves 23, as shown in FIG. 4 serves as a liquid source for the fluidic-devices. The sampling can happen via dipping of the fluidic elements 9 (only one element is shown) within the grooves (contact with the fluid). In doing so the capillarity(capillary force) of the bent elements has to be bigger than the one of the grooves, which are arranged on the disk. This may happen e.g. by using smaller capillary dimensions or bigger capillary aspect proportions.

To ensure, that the disk or the CD grooves are always filled with fluid, it is preferred to arrange etched well reservoirs 25. These wells may be filled with conventional methods, e.g. by using pipettes. The disk can be kept static or can be rotated so that sampling is possible at any location around the circular-like grooves.

Figure 4B:
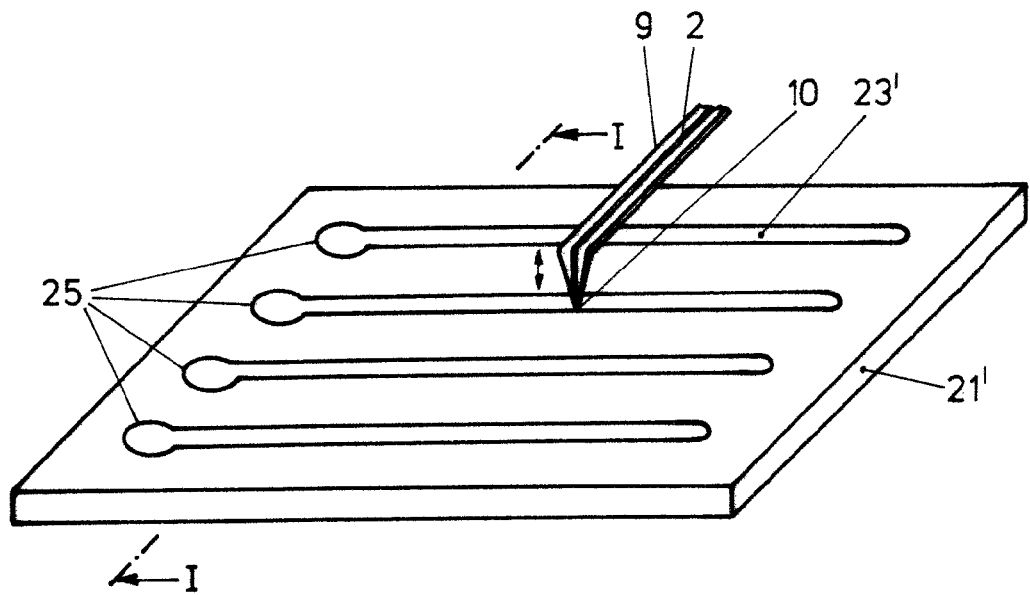

In FIG. 4b a similar panel-like well plate 21' is shown which in contrast to FIG. 4b does have straight-lined grooves 23' which are connected to edged well reservoirs 25. Again the collection of fluid samples can be executed by using fluidic elements 9 (only one element is shown) which are dipping into the grooves 23'. Similar to the disk-like plate 21 of FIG. 4a the panel-like plate 21' of FIG. 4b can be moved in longitudinal direction, so that sampling can be executed along the full length of the grooves 23'.

Figure 4C:
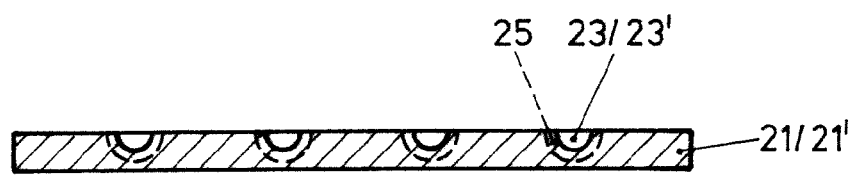

FIG. 4c shows a cross-sectional view along the line I'I from FIGS. 4a and 4b. It shows the dimensions of the wells 25 which are somewhat bigger than the dimensions of the respective grooves 23 or 23' respectively. As a consequence it is easy to fill these wells 25 and on the other hand by using the wells it is guaranteed, that the grooves 23 or 23' respectively are uniformly filled with the respective fluid media for sampling correction.

In FIG. 4 the advantage of the present invention or inventive device respectively is shown very clearly, as the bent fluidic elements can be guided over the disk parallel to the surface of the disk, so that the sampling can be executed even if the local dimension proportions are limited. In other words in case of using a conventional pipette the space above a well-plate disk 21 has to be open or free respectively, while in case of the use of an inventive fluidic element a relative small gap above the surface is already sufficient.

Figure 5:
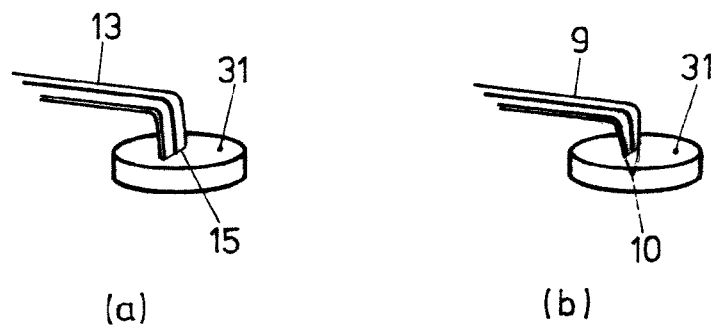
FIGS. 5a and 5b show in perspective view the simple immersion of a bent fluidic element into a fleece or non woven element.
Figure 6:
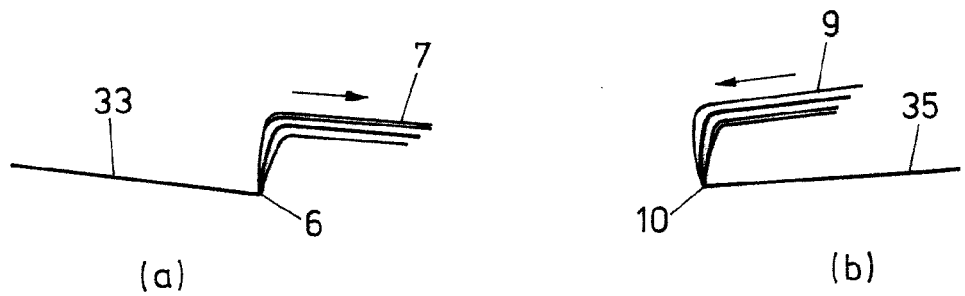
FIGS. 6a and 6b show schematically in perspective view the dispense of a fluid from a bent fluidic element in accordance with the principal of a fountain pen.

In the following FIGS. 5 to 7 possible examples of the disposal of a sample should be explained in more details. In the FIGS. 5a and 5b the disposal of a sample is executed by simply dipping a bent fluidic element into a fleece or nonwoven element 31. In FIG. 5a the disposal of a sample into the fleece 31 from a tip element 13 is shown, while in FIG. 5b the disposal of a sample into the fleece 31 is effected from a needle-shaped dip-end 9.

The disposal of a sample may also be effected by contact of the tip-like-end of the bent fluidic elements onto a plain surface, as shown in the FIGS. 6a and 6b. FIG. 6a shows the principal of a fountain pen using an element 7 with an inner open capillary. The fluidic element 7 is preferably drawn for producing the stripe 33 containing the disposed liquid. In contrast FIG. 6b shows the principal of a fountain pen using an element with an open outer capillary. The fluidic element 9 is preferably pushed to produce the stripe 35, containing the disposed liquid. But of course the fluidic element 7 may also be pushed while the fluidic element 9 may be drawn for the production of the respective stripes. Finally it should be mentioned, that the capillary at least in the area of the fountain pen like tip-end may also be formed in an open manner on both sides, which means, the capillary is open end-to-end analogue to a fountain pen, which is used e.g. for hand-writing.

Figure 7:
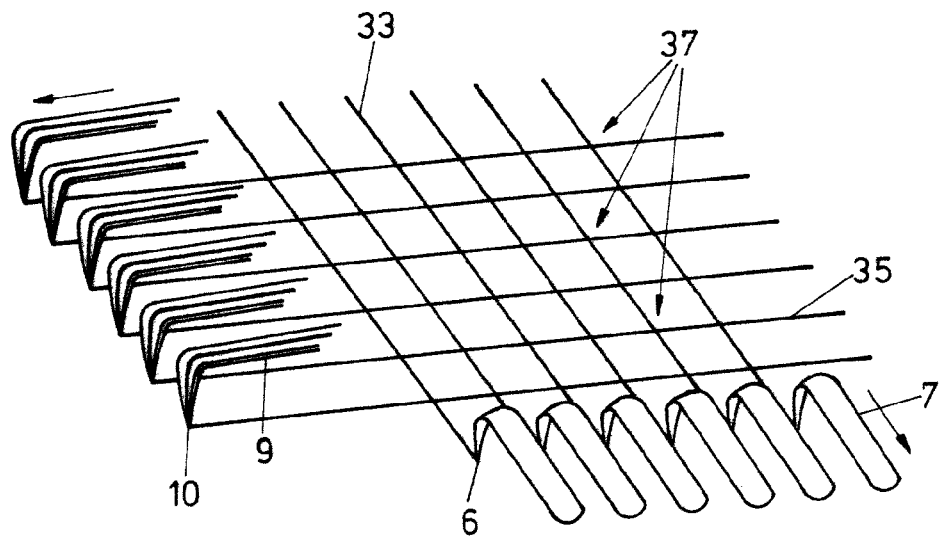
FIG. 7 shows schematically a so-called multiplex array with mixing zones, produced by the use of fountain pen like fluidic elements.

FIG. 7 shows schematically and in perspective view a so-called multiplex-array with N×M mixing zones.

To produce a N×M-array a plurality of so-called fountain-pen needles are used as schematically shown in FIG. 7. Needle elements 7 with open channels "inside" as well as bent needles 9 with open channels "outside" or needle tips with end-to-end open channels or capillaries may be used. By disposing the liquid from the needle tips 6 or 10 respectively the liquid stripes 33 and 35 can be drawn, the liquid lines are intersecting, so that mixed-zones 37 will occur. The shown configuration is as already mentioned above a so-called multiplex-array with N×M-mixing zones.

Figure 8:
FIGS. 8a and 8b show the sample transfer from fluidic device to fluidic device by overlapping contact of capillaries.
Figure 9:
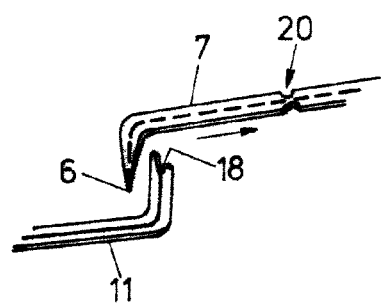
FIG. 9 shows schematically in perspective view the transfer of a fluid between two fluidic elements by use of additional positioning elements.

With reference to FIGS. 8 and 9 it should be shown, how the transfer of a sample from one fluidic device to another fluidic device may be executed. For that reason in FIG. 8a the transfer of a sample from a tip device 11 with a tip end 12 to a further tip device 11 with the tip end 12 is shown. The tip end 12 of the one device 11 is slipped over the opposed tip-end of the other device. It is important, that upon contact the two capillaries are overlapping. The one device is acting as a liquid source to the other empty device which acts as liquid acceptor. One condition is that the two devices which act comprise open capillaries, which are overlapping.

In FIG. 8b shows in analogue manner the sample transfer from one needle 7 with the tip end 6 to a tip element 11 with the tip end 12. The transfer is executed by moving horizontally of the one device until a contact of the two capillary channels is reached for the transfer of the liquid. So that the transfer can occur the capillarity (capillary force) of the one tip element has to be bigger than the one within the capillary of the needle. This can be achieved by using smaller capillary dimensions in the tip element or by bigger capillary aspect ratios.

In FIG. 9 a further possibility of the transfer of the liquid is shown. For that reason in one tip-like formed device 11 a channel 18 is formed to solve the problem of positioning. The needle-like device 7 is guided in a horizontal manner until the needle tip 6 engages into the positioning channel 18 and the transfer of the liquid may occur. In addition a narrowing portion 20 at the upper needle like device 7 can be arranged to allow an easier x/y-positioning. The positioning aids or positioning elements respectively can be integrated in a simple manner already e.g. within an etching mask. The individual bent elements may have additional structured portions such as e.g. groups or narrowing portions which enables the elements to engage in further elements or to compensate positioning inaccuracies between two elements. By using such positioning aids the safe transfer of fluids may be improved. The production of the mentioned auto-positioning or auto-adjusting structures is quasi free of charge and can e.g. be integrated already within the etching mask. For the production of the mentioned auto-positioning aids no further process steps are required. The elements include afterwards inherent those properties of the auto-adjustment and therefore no external auxiliary means are required anymore.

Figure 10:
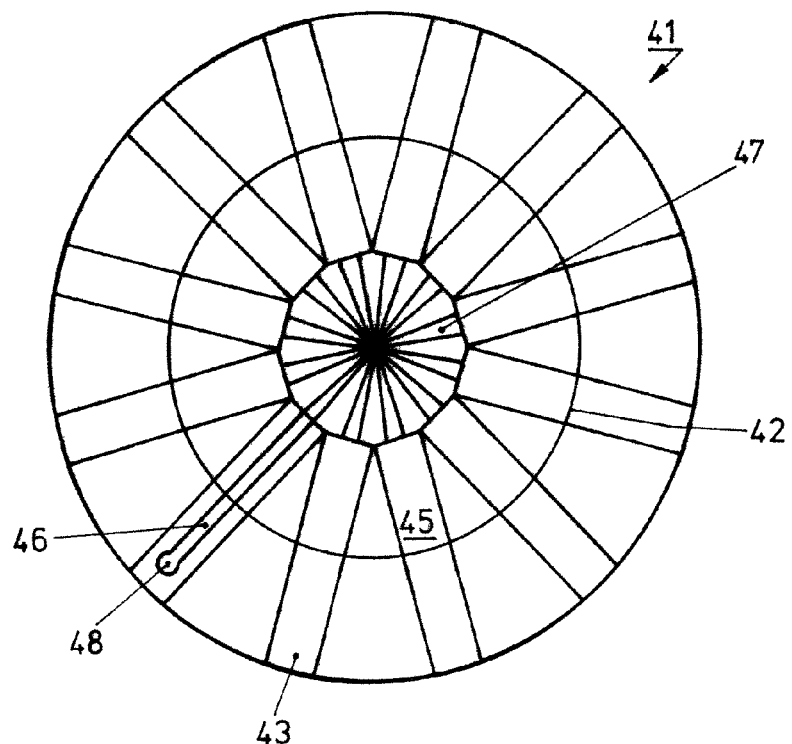
FIG. 10 shows in view from the top an example of a steel CD, etched on both sides, out of which for the production of an inventive structure needle shaped fluidic elements can be bent.

In FIGS. 1 to 9 only mainly individual fluidic elements are shown and in the following figures inventive structures should be explained in more details comprising a plurality of individual fluidic elements. For that reason FIG. 10 shows a CD-like steel disk 41, in which e.g. by etching or punching a structure is created provided for the production of a respective fluidic structure by bending the various individual elements. This structure is suitable for the sampling of various samples at the same time or the disposal of a plurality of samples at the same time. The cassetting problem can be solved in the same manner.

Figure 11:
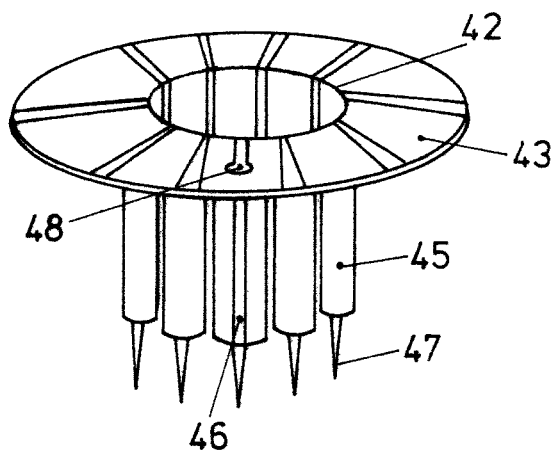
FIG. 11 shows the structure produced out of the CD of FIG. 10 from a side in perspective view.

A structure, produced out of the steel CD 41 in FIG. 10 is shown schematically and in perspective view in FIG. 11. The out-of-plane bent structure is shown from above and from the side. Within the CD-disk 41 the stripe-like length sections 43 and 45 are produced by etching as well as the needle-like tips 47 in the centre of the disk. By bending along the polygon-like bending edge 42 the inner sections of the stripes 45 are bent downwards and at the same time the needle-tips in the centre of the CD-disk 41 are separated simultaneously to produce the fluidic needle elements 47 extending from the ends of the stripes 45, which elements are provided for sampling or disposal of samples.

In addition and as shown with reference to one specific stripe preferably in the centre-line of the strip-like sections 43 and 45 capillaries 46, preferably again by etching are produced as well as in addition so-called pots or wells 48 in the area of the outer stripes 43.

By means of a structure as shown in FIG. 11 simultaneously a plurality of samples can be removed or sampled by dipping the needle tips 47 in respective sample grooves. The samples are collected from the tips of the needles 47, and transferred through the capillaries 46 into cavities or wells or pots 48 respectively. These enlarged reservoirs or pots, which are arranged on the disk-like sections 43 of the structure can be used for liquid sample detection or analysis such as e.g. by using infrared, NMR, etc.

Figure 12:
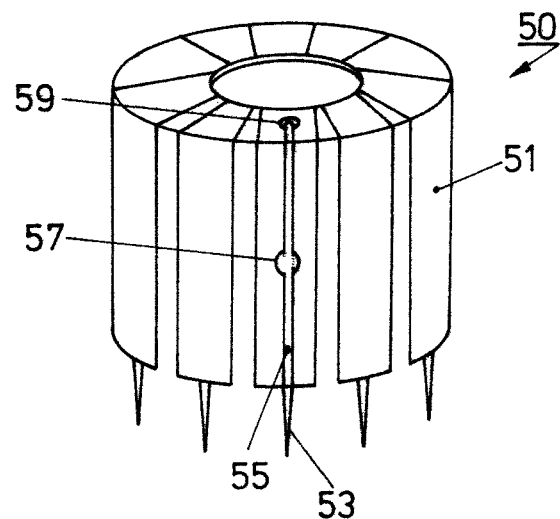
FIG. 12 shows a further structure similar to the one shown in FIG. 11

In analogue manner in FIG. 12 a further similar structure is shown in perspective view slightly from above, in which structure the strip-like sections 51 are arranged peripherally, which means at the outer outline of the structure 50. By using needle-like tips 53 again samples can be removed, which are transferred over capillaries 55 into reservoirs or pots or cavities 57 or 59 respectively. The detection or analysis respectively of the sampled samples can be executed in the periphery sections, which means in the reservoirs 57 as well as in the upper horizontal area in the reservoirs or pots or wells 59.

Figure 13:
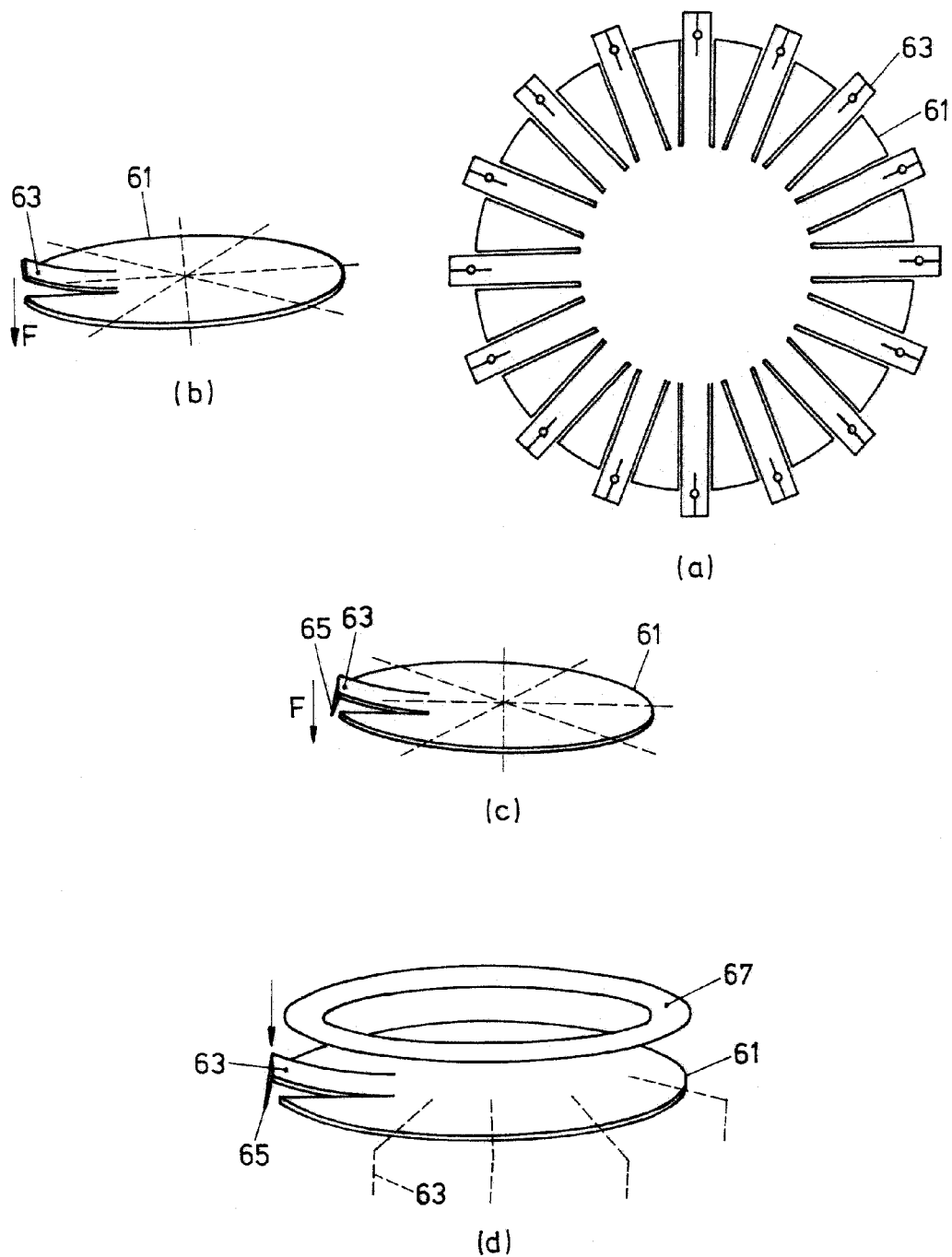
FIGS. 13a-13d show an elastic flat spring like fluidic element arranged on a CD in view from the top, in a sectional view seen from the side as well as actuated by use of an actuating element for the dispense of samples.

In the example according FIG. 11 a so-called drum-cassette "inside" and in FIG. 12 a so-called drum-cassette "outside" is shown. It is possible to bend a disk-shaped structure in such a way that a drum is formed. The structures, shown in FIGS. 11 and 12 are so-called drum-cassettes which means the two shown structures can solve the problem of cassetting as at the same it is possible to sample or to dispose a plurality of samples. The cassetting is therefore a collection of several elements collected in one piece. Also other shapes (other than drums) can be possible for cassetting, for example a crown or also a CD like shown in FIG. 13.

The cassette-like structures in addition have the advantage, that they can be stored or transported as e.g. stacks.

In FIGS. 13a to 13d a further embodiment of a possible inventive structure is shown comprising a plurality of fluidic elements, arranged on or at the structure. FIG. 13a shows in view from the top again an at least almost circular round metal disk or CD-like disk 61 at which peripherically extending the individual fluidic elements 63 are arranged. The individual fluidic elements can be produced by etching within the metal CD. As shown with reference to FIG. 13b the individual fluidic elements 63 are elastic flat-spring like elements with restoring force. To get a better general overview in FIG. 13b only one single fluidic element 63 is shown. The production of the flat spring like element is possible due to the mechanical elasticity of the metal material. As a result it is possible to produce specific activating principles such as the shown flatspring or solid body articulations.

FIG. 13c shows a possible specific embodiment the flat spring 63 being combined with a bent needle-like tip 65. The combination of the bent needle-like tip enables an improved sampling of samples.

In FIG. 13d schematically it is shown how a test strip contacting procedure can be achieved by use of a structure as shown in FIG. 13a. Again in FIG. 13d for a better overview only one pre-stressed fluidic element 63 having a needle-like tip 65 is shown. Further elements are only shown in outlines. The individual flat-spring-like elements 63 are slightly pre-bent in upward direction. By actuating e.g. with use of a circular actuating element 67 the individual flat spring like elements can be pushed downwards for contacting e.g. a test strip or a so-called well-plate disk, as shown e.g. in FIG. 4. Now either the sample sampling or the sample dispensing can be carried out and after the transfer of the fluid has been executed the actuation can be cancelled and the flat spring like elements 63 will return to their pre-stressed position, so that the test-strip is deblocked.

So that the fluidic elements or the individual flat springlike elements remain in their pre-stressed position for the production of the structure or the individual fluidic elements a material has to be used, which possesses certain elasticity or restoring force at deformation. Therefore in particular e.g. metal materials are suitable for the production of the proposed structures.

Furthermore it is also possible for actuating the fluidic elements or the flat spring-like elements to coat the metal substrate with a Piezo-substrat or a Bi-metal respectively, so that the actuation of the individual fluidic elements or flat spring-like elements can be executed by the movement of the Piezo-elements.

As already mentioned above the production of the flatspring-like elements can be achieved by etching what shall be explained in more details with reference to the attached FIGS. 14a and 14b. First again a metal CD or metal disk 81 is etched, so that the area or section 63 is partially separated from the metal disk.

As shown in FIG. 14b by applying a force F, the element is bent at its front end in opposed direction to the force F with a certain transmission ratio.

In other words the pre-stress occurs as described with reference to the FIG. 13a until 13d.

In addition the element, which is pre-bent with a certain transmission ratio, again, can be coated with a Piezo-substrate or Bi-metal, so that for sample-sampling or sample-disposal the activation is possible by means of the Piezo-element or bi-metal.

Figure 15:
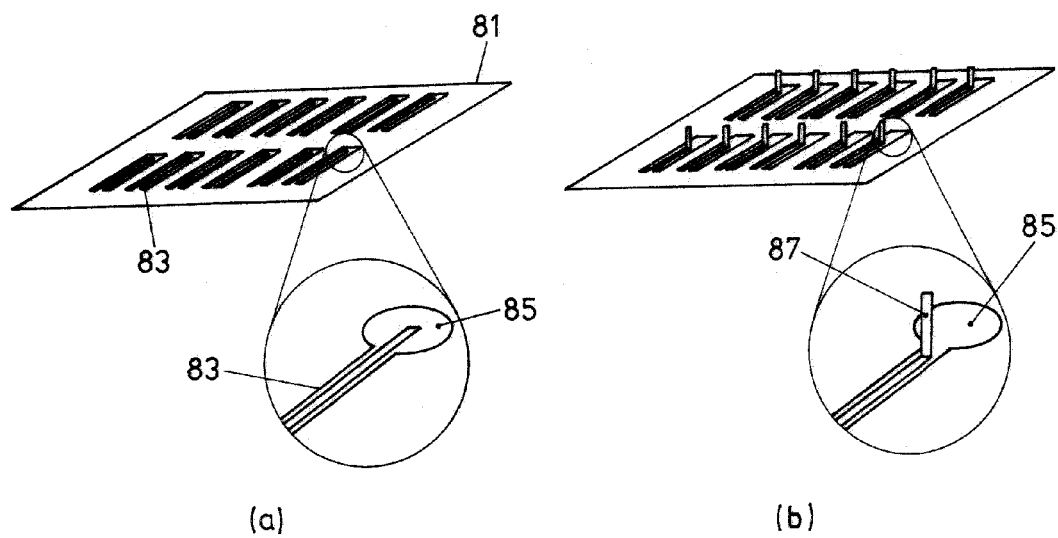
FIGS. 15a and 15b show a planar micro-structure produced in conventional manner as well as a bent "out-of-plane" micro-structure.
Figure 16:
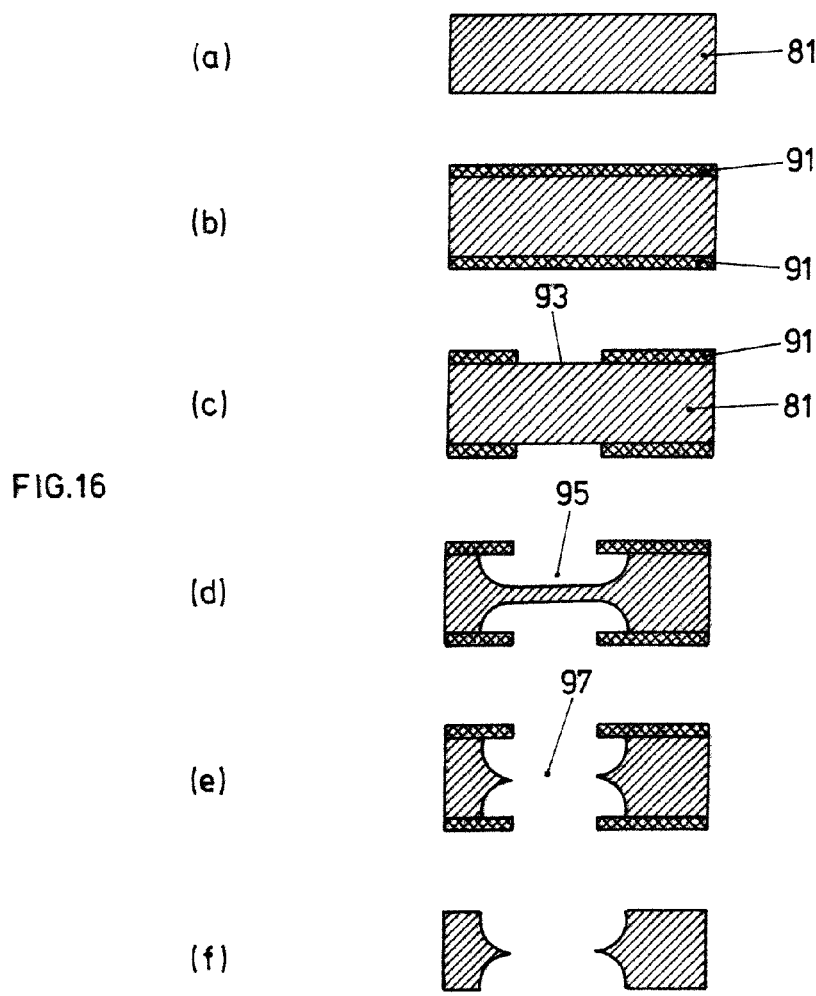
FIGS. 16a to 16f show a possible version for the production of fluidic channels in inventive fluidic elements.

With reference to the FIGS. 15 and 16 the production of inventive fluidic elements should be explained in more details. FIG. 15a shows a planar structure 81 for fluidic amounts in the nl and μl-range produced conventially, which means on a substrate 81 the nl or μl-stucture is produced by etching. At the respective ends of each element 83 comprising a channel or capillary 84 of the structure a hole or cavity 85 is provided, if needed, which is big enough for applying a bending tool.

FIG. 15b shows the bent out-of-plane nl or μl-structure 87, in which the individual elements 83 are bent out, forming the out-of-plane bent element parts 88, which may have a bend or deflection in the range of approximately 90 degrees. Of course the angle can be different and can be in the range of only a few degrees up to an angle of almost 180 degrees.

Figure 2:
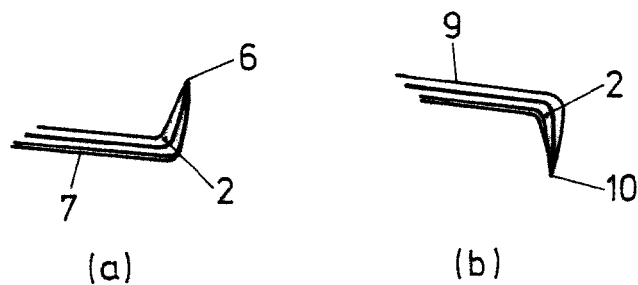
FIGS. 2a and 2b show in perspective view bent elements comprising a needle shaped tip-end.

The production of an individual structure element 83, comprising at least one fluidic channel 84 as described in particular with reference to the FIGS. 1 to 3 shall be described in more details with reference to FIG. 16a until 16f. FIG. 16a shows in cross-sectional-view a metal-substrate corresponding to the substrate-plate 81 from FIG. 15. Substrate materials, which have to be suitable for the applications according the present invention must have the inherent feature of plastic deformation, which means as a consequence e.g. metals or elastic polymers, are suitable. The use of rather brittle, fragile or amorphous materials such as e.g. silicon, glass, etc., is only limited, as deflection in the third dimension is practically not possible.

In FIG. 16b the metal substrate from FIG. 16a is coated e.g. on both sides with a polymer layer 91, as usually used with etching procedures.

The polymer layer afterwards is partially exposed to light and partially removed by washing of the exposed parts, so that channel-like longitudinal extending free areas 93 will occur, as schematically shown in FIG. 16*c*. By etching the metal the free areas 93 channel-like capillaries 95 will occur, as shown schematically in FIG. 16*d*. Of course the etching has not to be executed on both sides and therefore only one surface of the metal sheet may be treated for the production of a capillary channel 95 which is open on one side only.

According a further embodiment it is even possible to produce a totally open passage 97 by etching of the metal, as schematically shown in FIG. 16*e*.

Finally the polymer 91 shall be removed, so that the channel or capillary for an inventively proposed fluidic element is produced, as shown schematically in cross-section in FIG. 16*f*.

It is now possible to leave open the channel, as shown e.g. at the fluidic elements in FIGS. 1*b* and 1*c*. But on the other side it is also possible to cover or to bond the open channels e.g. by use of a cover film as e.g. a metal film, so that a closed channel will be produced.

Figure 14:
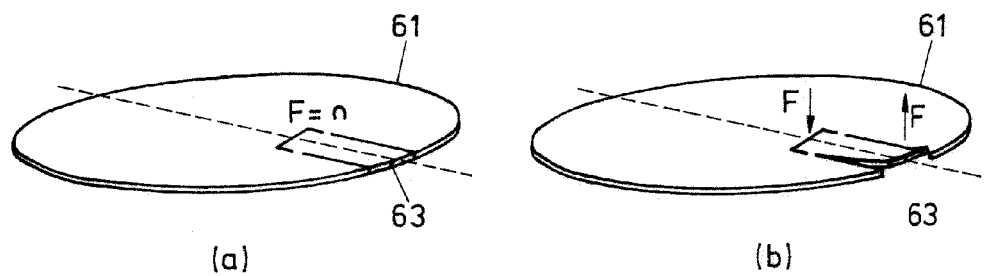
FIGS. 14a and 14b show an example of a mechanical transmission at flat springs for the production of a structure according the present invention.

At the same time at the production step of the channel-like capillaries by etching also transmission forces as described with reference to FIG. 14, integrated guidances as positioning elements, etc. can be produced.

Furthermore from simple planar nl or µl-structures certain parts can be bent out of the two-dimensional plane into the third dimension (out-of-plane) by bending such as by arching, forming, etc., so that the inventive structures in the nl or µl-range will occur. The planar nl or µl-structures can be produced with conventional, micro technological production methods, such as lithography or etching, as described with reference to FIGS. 15 and 16. To achieve the individual out of the plane bent elements 88 as shown in FIG. 15*b*, various techniques may be applied. The most common or obvious one is to simply press at least part of the element 83 out of the plane of the structure 81, e.g. by using a bending or punching tool. It is also possible to pull the element along a punching tool or an edge containing tool. A further possibility is to apply a roller like tool. Again a further possibility is to apply heat on one surface of the structure or at least of an element to create a tension force, so that the bending procedure occurs without the use of a specific bending tool. Furthermore, if e.g. a symmetric edging is applied during the production process of the channel or capillary like groove as described with reference to FIGS. 16*a* to 16*f*, also a certain tension force may be achieved, with the result of creating a bent out of the plane portion without the need of a specific bending tool.

The bent elements can fulfill various different functions, as e.g. contacting, needle-punching, reflecting, etc. Preconditions for bending an element out of the substrate plane is the at least partial etching through the whole substrate sheet, as in particular described with reference e.g. to FIGS. 13*a*, 13*b*, 14*b*, 15*a* and 15*b*. The "total-through-etching" makes it possible to produce the individual single bent elements.

Figure 17:
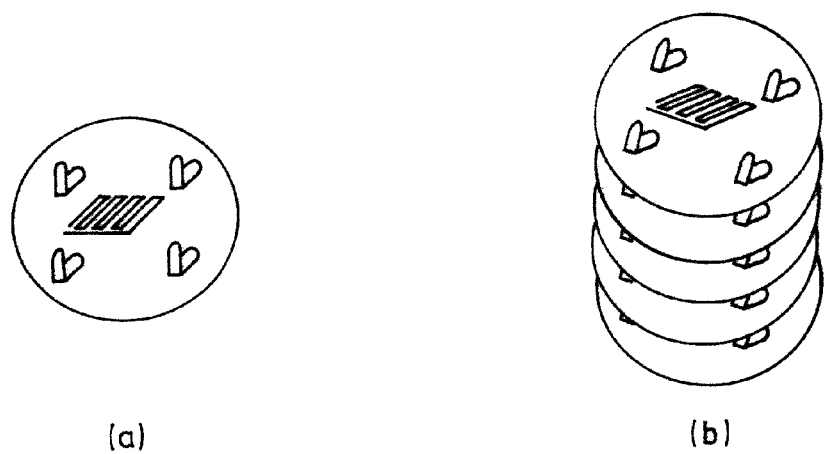

The possibility of plastic deformation of the micro-structure makes it possible to include inherent into the micro-fluidic systems e.g. out-of-plane distance-producing elements, positioning holes, adjustment aids, positioning aids, stoppers, etc. as schematically shown in FIG. 17*a*. This makes it possible to increase the improvement of e.g. the positioning of micro-fluidic elements in relation to an outside system. For the production of the mentioned adjustment or distance-producing elements no further process steps are required. If needed a further bending step has to be applied to bend those positioning elements or adjustment elements as the mentioned distance producing elements, as shown in FIG. 17*a* out-of-plane. But usually those elements as the distance producing elements may be integrated e.g. within the etching mask. The fluidic elements therefore include inherent those positioning elements or distance producing elements and no further external auxiliary means are required. Those auxiliary means in addition may include the fluidic channels or capillaries. In any case the fluid is flowing "around-the-corner". Therefore, it is possible to create a plate optimization (which means to reduce the fluidic area).

Furthermore, in FIG. 17*b* a stack of a plurality of micro-fluidic devices of FIG. 9, 17*a* is shown. In other words a plurality of micro-structures including distance-producing elements, stoppers, positioning holes, etc. can be stacked by an adequate positioning of those bent auxiliary parts. This makes it easier to create a cassetting of microstructures (with or without fluidic).

As already mentioned above the present invention refers to nl and µl-structures for the transport and/or the transfer of very small amounts of liquids in the nl and µl-range. As an example for sampling blood a needle like tip having a length of e.g. 3 mm can be used, the width of the needle-shaft may be approximately 400 µm, the capillary may have a width of approximately 200 µm and the depth of the capillary may be e.g. of about 80 µm. The amount of blood to be sampled can be in the range between 2 µl and 100 µl. These values are of course examples given for the better understanding of the present invention and therefore the present invention is not at all restricted to the mentioned values. It should be shown how fine or small respectively the inventively described micro structures are and witch small liquid amounts are taken into consideration in the present invention.

The big advantage of the present invention is that sampling or sample-disposal "around-the-corner" is possible with using the bent nano-or micro-structures. By using the inventive devices or elements respectively or structures sampling or sample-disposal is possible in spatial or dimensional very limited conditions, as e.g. a fluidic device can be guided or moved parallel to a substrate or object respectively, from which a sample has to be sampled, which simplifies essentially the sampling of a sample.

The fluidic elements and structures which are shown with reference to the FIGS. 1 to 17 as well as the described production methods are of course only examples and the present invention is not at all limited to the figures, shown elements and describes procedures. The figures are only used for the better understanding and in addition e.g. the used materials for the production of fluidic elements or structures respectively are of course not limited to metals or elastic polymers. It is also possible, that at least partially elastic ceramic-material can be used for the production of the inventive elements or structures respectively. Furthermore it is not essential, if open or closed capillaries are used, if at the ends of the liquid devices needle-like-tips, edgeless ends, straight cut end-tips, rounded or waved or serrated ends are arranged.

What is claimed is:

1. A device for sampling, transporting and/or disposal of fluid media via capillarity in the nanoliter (nl) to microliter (µl) range comprising a circular substrate defining a substrate plane and having at least one longitudinal extending strip like portion which is bent at least at one location out of the substrate plane, said strip like portion extends radially and is provided with a fluid channel which provides a capillary force to the fluid media when contacted therewith, wherein the longitudinal extending strip like portion is a spring-like element with an arcuate curve in the direction opposite the bend.

2. The device according to claim 1 wherein the fluid channel is open and arranged along the side of the strip like portion defining the inside surface of the bend of the strip like portion.

3. The device according to claim 1 wherein the fluid channel is open and is arranged along the side of the strip like portion defining the outside surface of the bend of the strip like portion.

4. The device according to claim 1 wherein the fluid channel is open and is arranged along the sides of the strip like portion defining the inside and outside surfaces of the bend of the strip like portion.

5. The device according to claim 1 wherein the strip like portion comprises at least one end to which the fluid channel is extended, said end is provided with a shape selected from the group comprising needle-like, straight-lined cut, and rounded.

6. The device according to claim 1 wherein at least the strip like portion is a deformable material comprising a metal, a polymer, and combination thereof.

7. The device according to claim 1 wherein the bent location has a bend-angle that is in the range between 60 and 120°.

8. The device according to claim 1 wherein the strip like portion is a plurality of the strip like portions provided on the substrate.

9. The device according to claim 1 wherein the strip like portion comprises at least one end to which the channel is extended, and wherein said end is resilient.

10. The device according to claim 1 wherein the fluid channel comprises a reservoir.

11. A structure containing the device according to claim 1.

12. The structure according to claim 11 wherein said strip like portion is a plurality of strip like portions and said structure comprises a plate having two or more individual grooves, said plate being provided adjacent said substrate such that said grooves is configured to be source of the fluid media for a respective fluid channel of said strip like portions.

13. A method for producing a device used to sample, transport and/or dispose fluid media via capillarity in the nanoliter (nl) to microliter (µl) range comprising:
providing a circular substrate which defines a substrate plane;
providing at least one longitudinal extending strip like portion within the substrate, said strip like portion extending radially, having at least one fluid channel and having an end; and
bending the longitudinal extending strip like portion at a location such that said end is out of the substrate plane.
wherein the longitudinal extending strip like portion is a spring-like element with an arcuate curve in the direction opposite the bend.

14. The method according to claim 13, wherein the substrate comprises as least one etched channel.

15. A device for sampling, transporting and/or disposal of fluid media via capillarity in the nonoliter (nl) to microliter (µl) range comprising a circular substrate defining a substrate plane and having at least one longitudinal extending strip like portion which is bent at a right angle at least at one location out of the substrate plane, said strip like portion extends radially and is provided with a fluid channel which provides a capillary force to the fluid media when contacted therewith, wherein the longitudinal extending strip like portion is a spring-like element with an arcuate curve in the direction opposite the bend.

16. The device according to claim 15 wherein the strip like portion is a plurality of the strip like portions provided on the substrate.

17. The device according to claim 15 wherein the fluid channel comprises a reservoir.

18. The device according to claim 15, wherein the fluid channel is open and is arranged along the side of the strip like portion defining the outside surface of the bend of the strip like portion.

* * * * *